United States Patent [19]
Blair

[11] Patent Number: 5,697,921
[45] Date of Patent: Dec. 16, 1997

[54] ANATOMICAL IRRIGATION BASIN

[76] Inventor: Jonathan B. Blair, 25242 Buckskin Dr., Laguna Hills, Calif. 92653

[21] Appl. No.: 522,176

[22] Filed: Aug. 31, 1995

[51] Int. Cl.$^6$ .............................. A61M 1/00; A61B 5/00
[52] U.S. Cl. ..................... 604/317; 604/319; 128/760; 4/450; D24/123
[58] Field of Search ........................... 604/317, 319, 604/321, 324, 329; 128/760, 761, 762, 769, 849; D24/121, 123; 4/450, 451

[56] References Cited

U.S. PATENT DOCUMENTS

| | | | |
|---|---|---|---|
| D. 46,262 | 8/1914 | Meinecke | D24/123 |
| D. 174,990 | 6/1955 | Horn, Jr. | D24/123 |
| D. 216,058 | 11/1969 | Painter et al. | D24/123 |
| 2,182,254 | 12/1939 | Farrell | 4/450 |
| 3,460,164 | 8/1969 | Patton | 4/451 |
| 3,609,771 | 10/1971 | Avoy | 4/451 |
| 3,992,729 | 11/1976 | Mills | 4/450 |
| 4,368,548 | 1/1983 | Glass | 4/451 |
| 5,069,878 | 12/1991 | Ehrenkranz | 128/760 |
| 5,487,393 | 1/1996 | Haswell et al. | 128/760 |

*Primary Examiner*—John G. Weiss
*Assistant Examiner*—David J. Cho
*Attorney, Agent, or Firm*—Michael G. Petit

[57] ABSTRACT

A basin adapted to receive and contain a fluid draining from an irrigated wound or abscess on a portion of a person's body. The basin is anatomically contoured and dimensioned to permit a fluid tight seal between the person's skin and the basin when a potion of the rim of the basin is in juxtaposition with a variety of contoured portions of the body such as the trunk, arm head, finger, neck, and the like. The basin consists of a bowl-like container having unitary construction and having a flat, substantially planar bottom portion. The perimeter of the bottom portion is trilobate, having a plurality of convex curves or lobes around the outer periphery thereof. The lobes are convex, projecting generally outward from the center of the bottom portion, each lobe having a different radius of curvature than the other lobes. The bottom portion of the basin is bounded by a smooth continuous wall projecting upward and slightly outward from the periphery of the bottom portion. Near the superior aspect or top of the wall, the wall curves gracefully outward and upward to form a peripheral rim flange around the top of the basin. The width or lateral extension of the rim flange varies along the periphery of the rim and provides means for holding the basin without exposing fingers to the content of the basin. The outermost edge of the rim flange is shaped to direct the flow of a fluid spilled thereon into the basin under the force of gravity rather than away from the basin as occurs with prior art basins having a recurved rim flange. The basin, which is multi-contoured to adapt to a variety of anatomical topographies, presents an overall shape operable for enabling the nested stacking of a number of such units to reduce storage space.

15 Claims, 3 Drawing Sheets

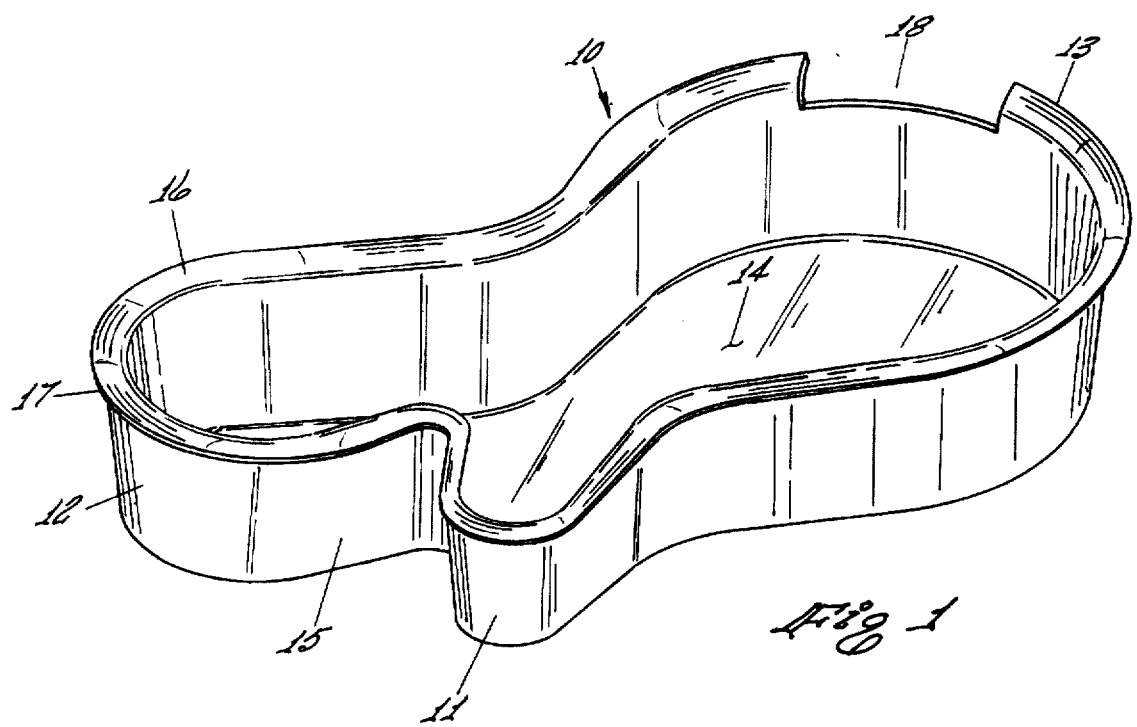
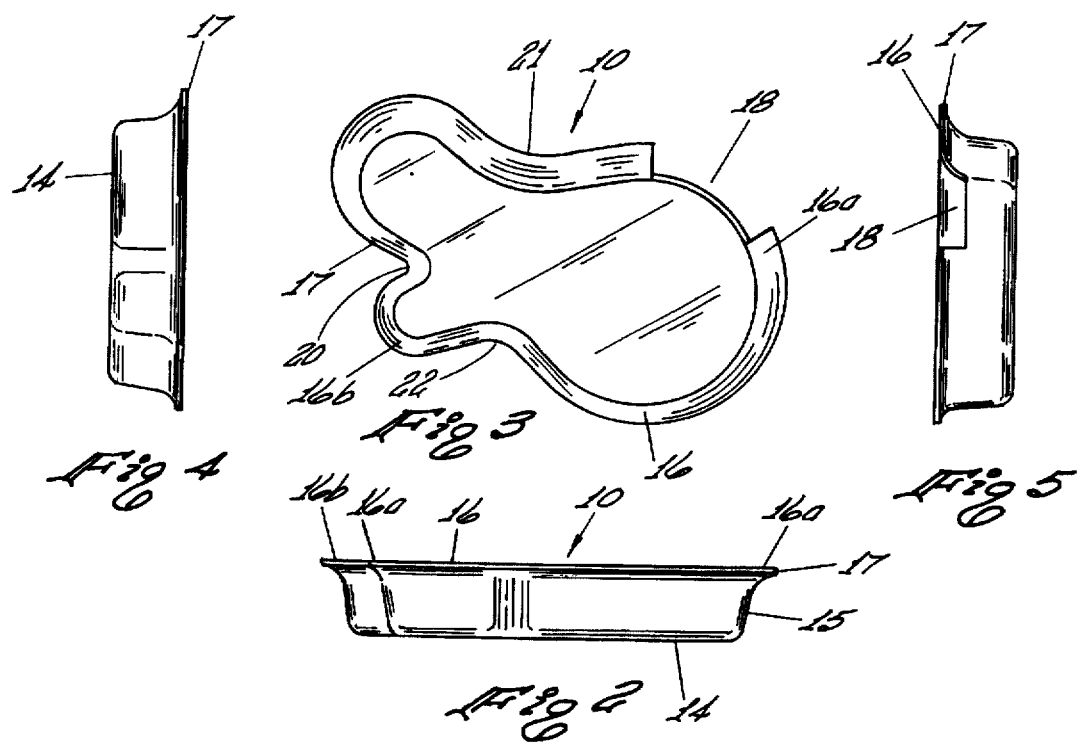

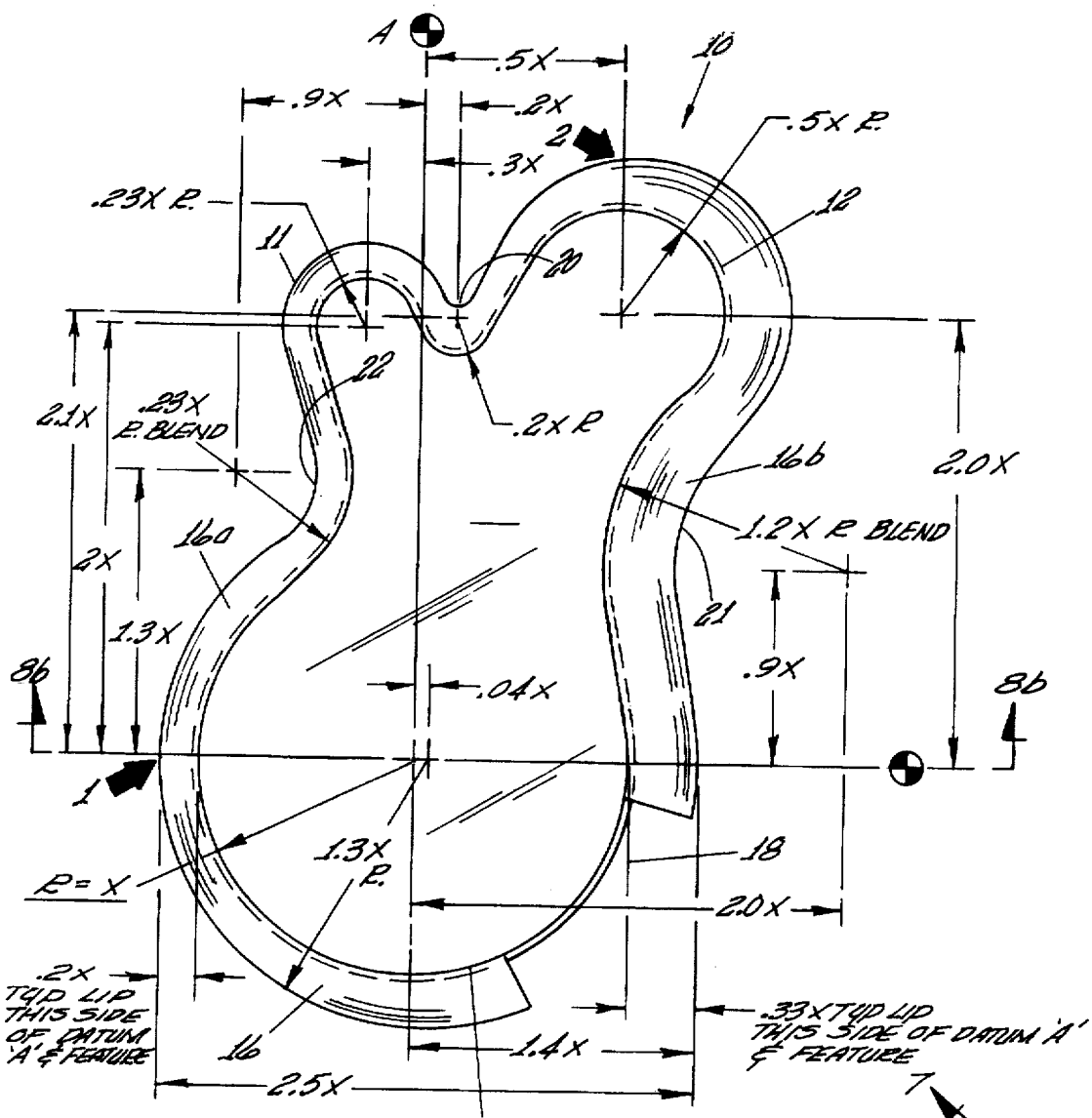
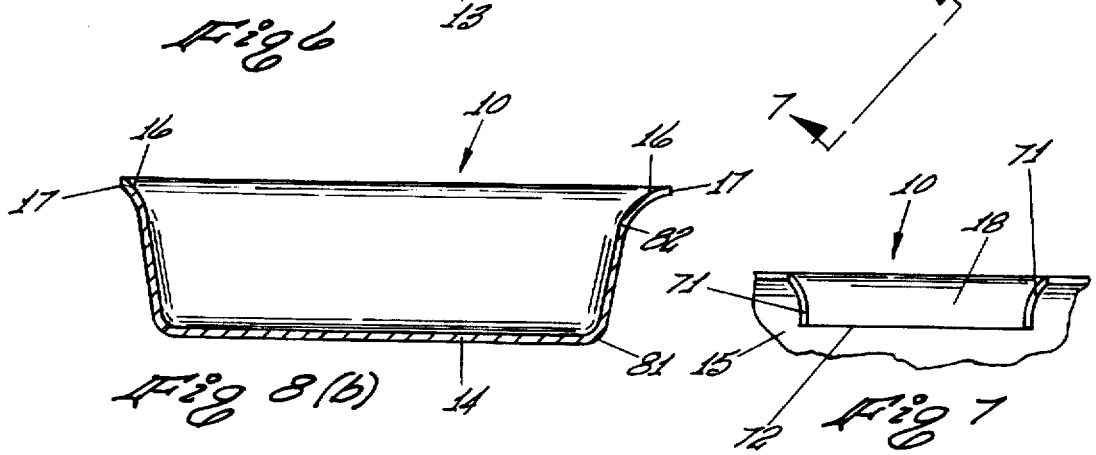

ANATOMICAL IRRIGATION BASIN

BACKGROUND OF THE INVENTION

1. Field of the Invention

This invention relates generally to a surgical basin for collecting wound irrigating fluids and the like, and more specifically to a contoured, anatomically conforming portable basin for catching and containing an irrigation fluid.

2. Prior Art

Emesis and/or kidney basins are commonly used in the hospital environment for collecting emesis, saliva, urine, wound irrigation fluids and the like. Such basins are normally stamped from a single piece of stainless steel or similar durable metal or molded from a suitable elastomer. Such unitary basins are common in the prior art and are generally characterized by a contoured wall and a bottom having a "kidney-shaped" curvature, the curvature permitting the wall and top rim of the basin to be pressed against, and anatomically conform to, certain areas of the body. Such anatomical conformation enables an irrigation fluid injected against a wound on a patient's body to drain into a basin pressed against the skin below the wound. Such a basin is described, for example, in U.S. Pat. No. 1,061,769 to Meinecke. Pierce, in U.S. Pat. No. 5,045,076, describes a disposable insulated surgical basin.

Surprisingly, although such irrigation basins have been employed in trauma care environments for many years, very little innovation has occurred. For example, basins in accordance with the prior art continue to have a "rolled down" or recurved upper skin-contacting rim which forms a more or less fluid-tight seal between the basin rim and the skin when pressed against a potion of the body. Fluid incident upon the rim is directed either into the bowl or towards the outside of the rim since the rim is recurved. The apex of the rim of prior art basins is not at the outer periphery of the rim and does not contact the skin. Such rim constructions permit spillage and do not provide means for a person to hold the basin without exposing his/her fingers to the contents of the basin. Accordingly there remains a need for a portable surgical basin for catching irrigation fluids which provides a fluid-tight anatomically conforming seal when the rim of the basin is pressed against the skin. The basin preferably should provide an outer rim which conforms to different portions of the body presenting various anatomical curvatures. Further, the basin should be shaped to enable stacking. In addition, there is also a need for a basin having means for accommodating and stabilizing those smaller portions of the body which are frequently lacerated, such as fingers, the wrists, or hands in a manner wherein the wound being irrigated is suspended over the bottom of the basin and stabilized.

SUMMARY OF THE INVENTION

An irrigation basin is provided having a substantially flat trilobate bottom with a contoured wall rising upward therefrom and forming the side thereof. The wall of the basin generally curves in and out around the periphery of the basin following the multilobate profile presented by the periphery of the bottom; each convex curve is followed by a concave curve as the perimeter of the bottom is traversed. The upper or topmost portion of the wall of the basin has a flange projecting laterally (outward) from the basin interior which flange terminates substantially at the apex of the wall. Thus, the flange unlike the "rolled down" or recurved rim of prior art basins, prevents the flow of irrigation fluid between the rim and the skin.

It is a first object of this invention to provide an irrigation basin having a skin-contacting outer rim, the rim having a plurality of anatomically conforming portions which may be selected to anatomically conform to and form a fluid tight contact with the skin of a patient.

It is another object of the invention to provide an irrigation basin having a flange along the periphery of the upper rim projecting laterally outward from the basin which directs a fluid flowing thereonto into the basin and having a different lateral extension on one side of the basin than on the other which flange permits the basin to be supported without exposing the supporting hand to the contents of the basin.

It is yet another object of this invention to provide an irrigation basin having unitary construction and which may be stacked one upon the other to conserve storage space.

It is yet another object of this invention to provide an irrigation basin having volumetric fluid measuring means integral therewith.

It is a further object of this invention to provide an irrigation basin having the foregoing attributes and features and further wherein the irrigation basin may be inexpensively manufactured.

It is another object of this invention to provide an irrigation basin which is disposable and biodegradable.

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

BRIEF DESCRIPTION OF THE DRAWINGS

FIG. 1 is a perspective view of the preferred embodiment of the irrigation basin of the present invention.

FIG. 2 is an front elevational view of the embodiment of the irrigation basin in FIG. 1.

FIG. 3 is a top plan view of the irrigation basin of FIG. 1.

FIG. 4 is an end on elevational view of the irrigation basin of FIG. 3 when viewed from left to right.

FIG. 5 is similar to FIG. 4 and shows an end on elevational view of the irrigation basin of FIG. 3 when viewed from the right to left.

FIG. 6 is a top plan view of the irrigation basin of FIGS. 1 and 3 showing preferred angles of radii for the convex lobes in the bottom and wall and exemplary dimensions for the irrigation basin.

FIG. 7 shows a partial elevational view of an embodiment of the basin having a notched portion in the wall of the irrigation basin and shown in FIG. 6 when viewed along line 7—7.

FIG. 8b is a cross sectional view of the irrigation basin of FIG. 6 along section line 8b—8b.

DESCRIPTION OF THE PREFERRED EMBODIMENTS

Figure 8A:
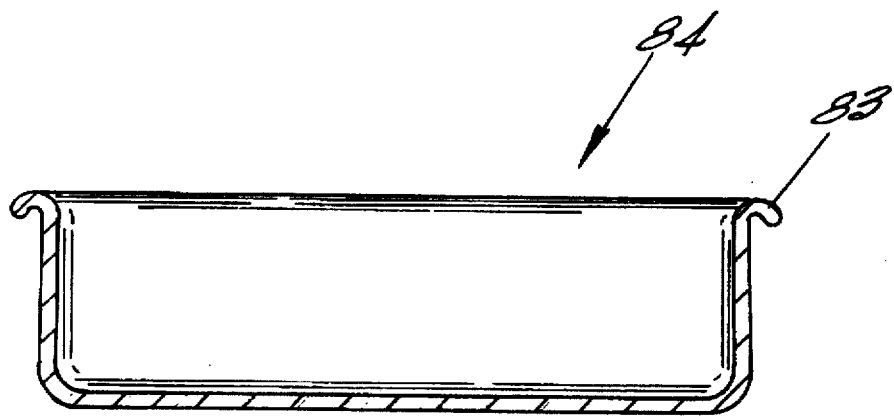
FIG. 8a shows a prior art basin having a recurved rim.

FIG. 1 is a perspective view of a first preferred embodiment 10 of an irrigation basin in accordance with the present invention. The curved, trilobate outer perimeter of the bottom 14 of the basin 10 rises upward to form the wall 15 of the basin. The wall 15 functions as a trilobate fluid containment barrier enclosing the bottom 14 and having a small lobe 11, a medium lobe 12, and a large lobe 13. The wall 15, which may be opaque or transparent, preferably has volumetric indicator marks (not shown) thereon to enable a volume of fluid (not shown) contained within the basin to be measured. The lobes 11, 12, and 13 are convex protuberances in the wall 15 and present a smoothly contoured wall; flowing together smoothly and continuously. Lobes 11 and 12 are separated by indent area 20, lobes 12 and 13 are separated by indent area 21, and lobes 13 and 11 are separated by indent area 22. The inferior (bottom-most) aspect of the trilobate wall 15 of the basin 10 projects upward and slightly outward from the curved periphery of the bottom 14. Near the superior aspect of the wall 15, the outward curve of the wall 15 becomes more exaggerated to form a flange 16 around the rim of the basin, the flange terminating laterally in an outer rim edge 17. A notch 18 (optional) in the wall 15 of the basin 10 is dimensioned to enable a person's wrist to be placed therein and be positionally stabilized by the notch while the person's (wounded) hand is suspended above the basin during wound irrigation.

Turning next to FIG. 3, the basin of FIG. 1 is shown as viewed from above. The perimeter of the basin 10 is seen to be trilobate, having the general outline or profile of a mitten. A side elevational view of the basin 10 is shown in FIG. 2. The wall 15 of basin 10 is seen to taper upward (and slightly outward) from the bottom 14 around the entire periphery of the basin to permit nested stacking of a plurality of identical basins. The width of the flange 16 is shown to be larger on the right side of the basin (16a) than on the left portion of the basin (16b). End-on elevational views of the basin in FIG. 3 viewed from the left and the right appear in FIGS. 4 and 5 respectively.

With reference now to FIG. 6, a top plan view of a preferred embodiment of the irrigation basin of the present invention is shown in detail. For the purpose of providing an example, the various dimensions of the irrigation basin 10 are shown with reference to a center line A, which center line A substantially bisects the bottom 14 of the basin, passing slightly to the left of the center of curvature of lobe 13. Line A serves as a convenient reference for identifying the position of a center point for the radius of curvature of each of the lobes of the trilobate bottom 14. The preferred radius of curvature for lobe 11 is about $^{11}/_{16}$". For lobe 12, $1\frac{3}{8}$" is preferred. Lobe 13, the largest, has a radius of curvature of about $3\frac{3}{4}$". Of course, the basin may be made larger or smaller in which case the radius of curvature of lobes 11 and 12 are given as a fraction of R (=X), the radius of curvature of the largest lobe 13. As noted above, lobes 11 and 12 are separated by indent area 20, lobes 12 and 13 are separated by indent area 21, and lobes 13 and 11 are separated by indent area 22. Indent area 20 has the smallest radius of curvature, indent area 21 has the largest radius of curvature, and indent area 22 has an intermediate size radius of curvature. Indent areas 21, 22, and 23, each having a different radius of curvature, are ideally suited to fit any part of the body placed there against. The flange 16 is seen to be substantially broader at the apical (superior aspect) portion of the rim on the right side of the basin, shown at 16b in FIG. 6, between the lobes 12 and 13, attaining a width or lateral extension of about 1" beyond the periphery of the bottom portion thereunder. The flange 16 narrows to approximately one-half inch on the portion of the outer rim of the basin at broad arrow 1 between lobes 13 and 11. Between lobes 11 and 12, the flange broadens rapidly to its full width at broad arrow 2. The broadest width of the flange is one inch on the right side (at 16b) and rapidly tapers down to one half inch at 16a on the left side of FIG. 6.

The notch 18 (optional) is seen more clearly in FIG. 7. The notch 18 comprises an indentation in the superior portion of the wall 15 of the basin 10, and is preferably dimensioned to accommodate the wrist or finger of a person therein. The smooth lateral walls 71 of the notch 18, along with the bottom edge 72 of the notch, serve to receive and stabilize an extremity such as a wrist or ankle placed therein while a wound or the like on the extremity to overly the basin during irrigation of the wound.

FIG. 8b shows an elevational view of the basin of FIG. 6 along section line 8b—8b. The portion 16b of the flange 16 appearing on the right is seen to be broader than the portion of the flange 16a appearing on the left. The bottom 14 of the basin is flat, preferably angled at the corners 81 and 82. More particularly the outer lateral edge 17 of the flange 16 is not recurved as in the rim 83 of a prior art basin 84 (FIG. 8(a). Since the rim of the present basin is not recurred, fluid (not shown) impinging upon the flange 16 is preferably directed into the basin 10.

Figure 9:
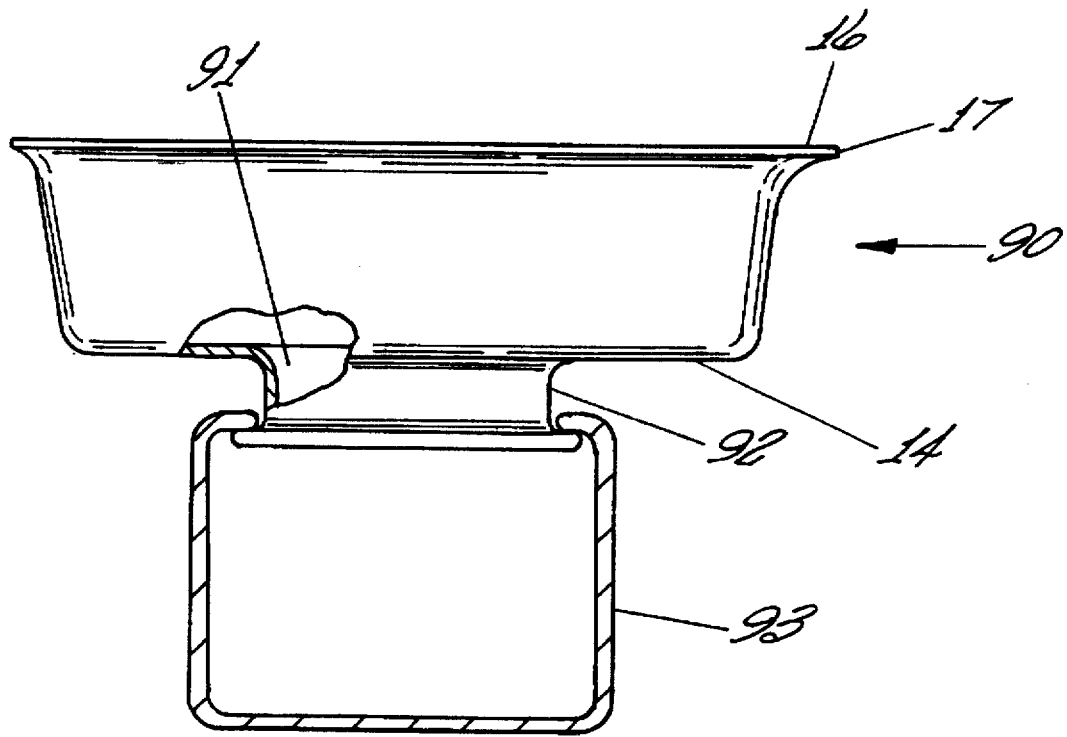
FIG. 9 is a partially cutaway side elevational view of an embodiment of the basin adapted for use with a sealable, disposable collection bag.

FIG. 9 shows a second preferred embodiment 90 of the basin including a collection bag 93 attachment means affixed to the bottom 14. A hole 91 in the bottom 14 of the basin 90 is encircled by a bag attachment means comprising a flange 92 adapted to releasably receive and hold the open end of a sealable collection bag 93. Following use, the bag 93 is removed from the basin 90, sealed and disposed of. The various embodiments of the basin in accordance with the present invention can preferably be made in one piece; that is, be of unitary construction, from a variety of moldable, formable or shapeable materials such as synthetic plastic polymers, natural biogenic polymers such as cellulose, chitron or a sheet metal. The material may be biodegradable.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A basin comprising (a) a substantially planar bottom portion bounded by a perimeter having three convex lobes projecting laterally from said bottom portion and wherein each of said three convex lobes has a radius of curvature which is different from the radius of curvature of any other of said bottom portion and continuous therewith, (b) a wall portion projecting upward and outward from the perimeter of said bottom portion and continuous therewith, and (c) a flange portion comprising a lateral extension of the superior aspect of said wall portion to form a rim in said wall portion.

2. The basin in claim 1 wherein the lateral extension of said flange with respect to said perimeter of said bottom portion varies around the perimeter of the wall.

3. The basin of claim 1 further comprising a region along wall portion without a rim and defining a notch in said wall portion.

4. The basin of claim 2 further comprising a region along wall portion without a rim and defining a notch in said wall portion.

5. The basin of claim 1 wherein said bottom portion has a hole therein and means operable for releasably attaching a collection bag to said bottom portion, the attached collection bag thereafter enclosing said hole in said bottom portion.

6. The basin of claim 2 wherein said bottom portion has a hole therein and means thereon operable for receiving and releasably attaching a collection bag to said bottom portion, the attached collection bag thereafter enclosing said hole in said bottom portion.

7. The basin of claim 3 wherein said bottom portion has a hole therein and means thereon operable for receiving and releasably attaching a collection bag to said bottom portion, the attached collection bag thereafter enclosing said hole in said bottom portion.

8. The basin of claim 1 wherein said rim has an outermost edge which forms an apex of said rim.

9. The basin of claim 8 wherein said rim extends upwardly and outwardly away from said wall portion, and slants downwardly from said apex.

10. A basin comprising (a) a substantially planar bottom portion bounded by a perimeter having three convex lobes projecting laterally from said bottom portion and wherein each of said three convex lobes has a radius of curvature which is different from the radius of curvature of any other of said bottom portion and continuous therewith, (b) a wall portion projecting upward and outward from the perimeter of said bottom portion and continuous therewith, and (c) a flange portion comprising a lateral extension of the superior aspect of said wall portion to form a rim in said wall portion which is displaced away from said wall portion, wherein said rim has an outermost edge which forms an apex of said rim, and said rim slants downwardly and inwardly from said apex.

11. The basin of claim 10 wherein the lateral extension of said flange with respect to said perimeter of said bottom portion varies around the perimeter of said wall.

12. The basin of claim 10 further comprising a region along wall portion without a rim and defining a notch in said wall portion.

13. The basin of claim 10, wherein said bottom portion has a hole therein and means operable for releasably attaching a collection bag to said bottom portion, the attached collection bag thereafter enclosing said hole in said bottom portion.

14. A basin comprising (a) a substantially planar bottom portion bounded by a perimeter having three convex lobes projecting laterally from said bottom portion and wherein each of said three convex lobes has a radius of curvature which is different from the radius of curvature of any other of said bottom portion and continuous therewith, (b) a wall portion projecting upward and outward from the perimeter of said bottom portion and continuous therewith, and (c) a flange portion comprising a lateral extension of the superior aspect of said wall portion to form a rim in said wall portion which is displaced away from said wall portion and which varies is width around said perimeter of said wall, and wherein said rim has an outermost edge which forms an apex of said rim, and said rim slants downwardly and inwardly from said apex, and wherein a portion of said wall portion does not have a rim and defines a notch.

15. The basin of claim 14, wherein said bottom portion has a hole therein and means operable for releasably attaching a collection bag to said bottom portion, the attached collection bag thereafter enclosing said hole in said bottom portion.

* * * * *